US012343279B2

(12) United States Patent
Bantwal et al.

(10) Patent No.: US 12,343,279 B2
(45) Date of Patent: Jul. 1, 2025

(54) BRACKET ASSEMBLIES INCLUDING RESTRAINT BRACKETS FOR PERSON SUPPORT APPARATUSES AND PERSON SUPPORT APPARATUSES COMPRISING THE SAME

(71) Applicant: Hill-Rom Services, Inc., Batesville, IN (US)

(72) Inventors: Gautham Kamath Bantwal, Batesville, IN (US); Jeyakumar Thiruppathi, Batesville, IN (US); Nicholas Batta, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 392 days.

(21) Appl. No.: 17/847,621

(22) Filed: Jun. 23, 2022

(65) Prior Publication Data
US 2023/0025593 A1    Jan. 26, 2023

Related U.S. Application Data

(60) Provisional application No. 63/225,593, filed on Jul. 26, 2021.

(51) Int. Cl.
*A61F 5/37* (2006.01)
*A61G 7/05* (2006.01)

(52) U.S. Cl.
CPC .............. *A61F 5/3776* (2013.01); *A61G 7/05* (2013.01)

(58) Field of Classification Search
CPC .... A61F 5/3776; A61F 5/3761; A61F 5/3784; A61F 5/3769; A61G 7/05; A61G 13/101; A61G 13/1245; A61G 2200/327; A44B 11/20; F16B 2/12; F16B 2/185; F16B 7/18; F16B 2/14; F16B 7/0493; A61B 2090/571; F16M 13/022
See application file for complete search history.

(56) References Cited

U.S. PATENT DOCUMENTS

| 4,729,138 A | 3/1988 | Heyman et al. |
| 5,433,222 A | 7/1995 | Boomgaarden et al. |
| 9,022,334 B1 * | 5/2015 | DeMayo .............. A61G 13/101 248/229.24 |
| 10,786,386 B2 | 9/2020 | Tao et al. |

(Continued)

FOREIGN PATENT DOCUMENTS

| CN | 107041806 A | 8/2017 |
| EP | 3 400 921 A1 | 11/2018 |

OTHER PUBLICATIONS

Extended European Search Report for Appl. No. 22186529.8 dated Dec. 5, 2022, 8 pages.

*Primary Examiner* — Ophelia A Hawthorne
(74) *Attorney, Agent, or Firm* — Dinsmore & Shohl LLP (57) ABSTRACT

A restraint bracket of a bracket assembly mounted to a lower surface of a support frame of a person support apparatus is disclosed. The restraint bracket includes a bracket body having an upper surface and a lower surface opposite the upper surface, a pair of flanges formed on the upper surface of the bracket body, and an attachment member extending from the lower surface of the bracket body, the attachment member having a first end and a second end opposite the first end, the first end and the second end fixed to the lower surface of the bracket body.

15 Claims, 7 Drawing Sheets

(56) References Cited

U.S. PATENT DOCUMENTS

| | | |
|---|---|---|
| 10,874,571 B2* | 12/2020 | Zahynacz ............ A61G 13/101 |
| 10,952,914 B1* | 3/2021 | Miller ................ A61G 13/1245 |
| 2010/0077549 A1 | 4/2010 | Hensley et al. |
| 2016/0296401 A1* | 10/2016 | Cole ..................... A61F 5/3776 |
| 2017/0165097 A1 | 6/2017 | Patmore et al. |
| 2017/0312113 A1 | 11/2017 | Acuna et al. |
| 2019/0374371 A1 | 12/2019 | Richardson |

* cited by examiner

BRACKET ASSEMBLIES INCLUDING RESTRAINT BRACKETS FOR PERSON SUPPORT APPARATUSES AND PERSON SUPPORT APPARATUSES COMPRISING THE SAME

CROSS-REFERENCE TO RELATED APPLICATION

This application claims the benefit of U.S. Patent Application Ser. No. 63/225,593, filed Jul. 26, 2021, for "Bracket Assemblies Including Restraint Brackets For Person Support Apparatuses And Person Support Apparatuses Comprising The Same," which is hereby incorporated by reference in its entirety including the drawings.

TECHNICAL FIELD

The present specification generally relates to brackets for securing a restraint strap to a support frame and, more specifically, bracket assemblies for securing a restraint strap to a support frame out of reach from a person atop the support frame.

BACKGROUND

Medical patients oftentimes need to be restrained to avoid causing immediate physical injury to themselves or others. As such, the arms and/or legs of the patient may be restrained using a restraint device such as, for example, one or more straps secured to the wrists and/or ankles of the patient at one end and having an opposite end secured to a support frame on which the patient is supported. The support frame may be a portion of a hospital bed, a stretcher, a chair, or similar support apparatuses commonly found in care facilities.

Accordingly, a need exists for improved restraint devices that permit restraining a person in an arm-up position while on a support apparatus.

SUMMARY

In one embodiment, a restraint bracket includes a bracket body having an upper surface and a lower surface opposite the upper surface, a pair of flanges formed on the upper surface of the bracket body, and an attachment member extending from the lower surface of the bracket body, the attachment member having a first end and a second end opposite the first end, the first end and the second end fixed to the lower surface of the bracket body.

In another embodiment, bracket assembly includes a restraint bracket including a bracket body having an upper surface and a lower surface opposite the upper surface, a plurality of bracket holes formed in the bracket body, a pair of flanges formed on the upper surface of the bracket body, and an attachment member extending from the lower surface of the bracket body, the attachment member having a first end and a second end opposite the first end, the first end and the second end fixed to the lower surface of the bracket body, a reinforcement plate having a plurality of plate holes corresponding to the plurality of bracket holes, and a plurality of fasteners extending through the plurality of bracket holes and the plurality of plate holes for attaching the reinforcement plate to the restraint bracket.

In yet another embodiment, a person support apparatus includes a support frame having an upper surface and a lower surface opposite the upper surface, and a restraint bracket mounted to the lower surface of the support frame, the restraint bracket including a bracket body having an upper surface and a lower surface opposite the upper surface, a pair of flanges formed on the upper surface of the bracket body, and an attachment member extending from the lower surface of the bracket body, the attachment member having a first end and a second end opposite the first end, the first end and the second end fixed to the lower surface of the bracket body.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Embodiments described herein are directed to person support apparatuses including a restraint bracket for restraining a person to a support frame in an arm-up position such that the arm or arms of the person may be restrained while extending in a direction toward the head of the person rather than along the person's side toward the person's feet.

The person support apparatuses include a support frame and a restraint bracket mounted to a lower surface of the support frame, the restraint bracket including a bracket body, a pair of flanges formed on the upper surface of the bracket body, and an attachment member extending from a lower surface of the bracket body. Various embodiments of the person support apparatuses and the operation of the person support apparatuses are described in more detail herein. Whenever possible, the same reference numerals will be used throughout the drawings to refer to the same or like parts.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Directional terms as used herein—for example up, down, right, left, front, back, top, bottom—are made only with reference to the figures as drawn and are not intended to imply absolute orientation.

Unless otherwise expressly stated, it is in no way intended that any method set forth herein be construed as requiring that its steps be performed in a specific order, nor that with any apparatus specific orientations be required. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

As used herein, the singular forms "a," "an," and "the" include plural referents unless the context clearly dictates otherwise. Thus, for example, reference to "a" component includes aspects having two or more such components, unless the context clearly indicates otherwise.

Figure 1:
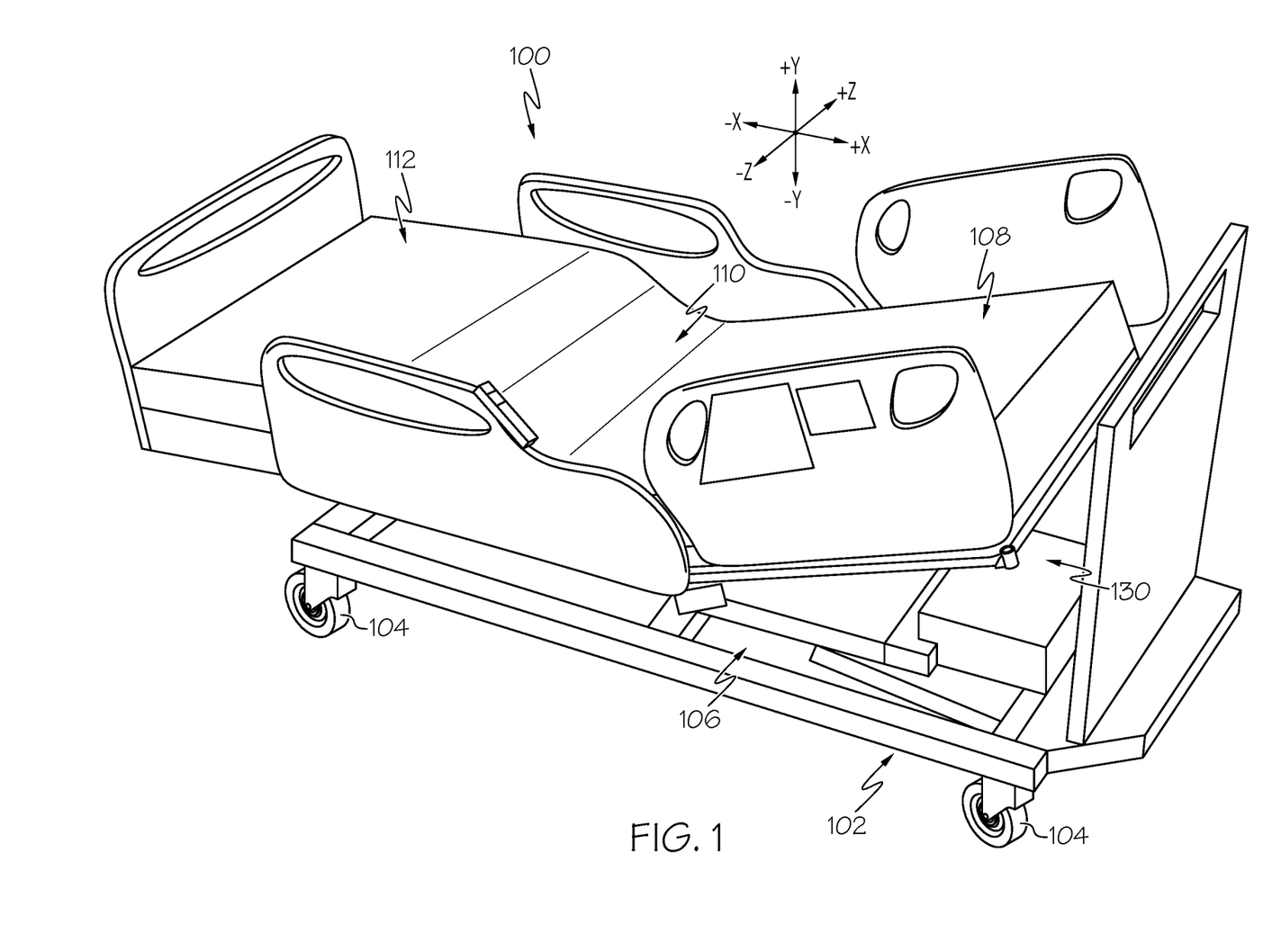
FIG. 1 schematically depicts a perspective view of a person support apparatus, according to one or more embodiments shown and described herein.

Referring now to FIG. 1, a person support apparatus 100 is illustrated according to one or more embodiments described herein. The person support apparatus 100 can be, for example, a hospital bed, a stretcher, a subject lift, a chair, an operating table, or similar support apparatuses commonly found in hospitals, nursing homes, rehabilitation centers, or the like. As shown in FIG. 1, the person support apparatus 100 includes a base frame 102 including a plurality of casters or wheels 104 that are movable along a ground surface. Although not shown, one or more lift members may extend from the base frame 102 and support a support frame 106 positioned above the base frame 102. Accordingly, a first end of each lift member is coupled to the base frame 102 and an opposite end of each lift member is coupled to the support frame 106. Thus, the support frame 106 is supported by the lift members above the base frame 102 such that the support frame 106 is movable relative to the base frame 102. In embodiments, the ends of the lift members may be rotatably attached to the base frame 102 and the support frame 106 to allow the ends of the lift members to rotate relative to the base frame 102 and the support frame 106 as the support frame 106 is raised. In embodiments, the support frame 106 has a head section 108, a seat section 110, and a foot section 112, with the seat section 110 located between the head section 108 and the foot section 112. The head section 108 and the foot section 112 are rotatable relative to the seat section 110. As described in more detail herein, the person support apparatus 100 includes one or more bracket assemblies 130 for attaching a strap to the support frame 106.

Figure 2:
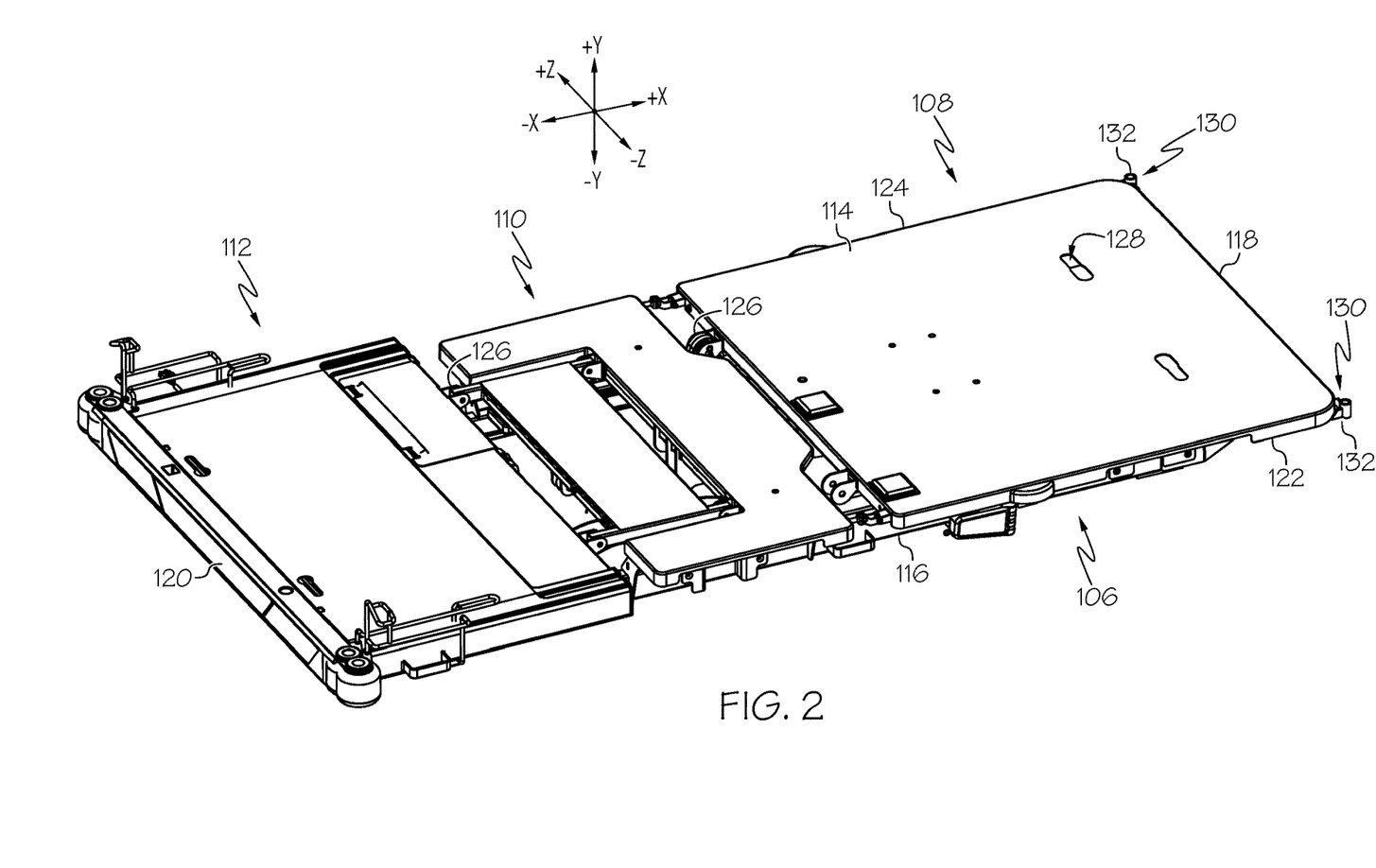
FIG. 2 schematically depicts a support frame of the person support apparatus of FIG. 1 including a plurality of bracket assemblies, according to one or more embodiments shown and described herein.

Referring to FIG. 2, the support frame 106 of the person support apparatus 100 is illustrated separate from the base frame 102. The support frame 106 has an upper surface 114, a lower surface 116 opposite the upper surface 114, a first or head end 118 at the head section 108, a second or foot end 120 at the foot section 112 opposite the head end 118, a first side 122 extending between the head end 118 and the foot end 120, and a second side 124 opposite the first side 122 extending between the head end 118 and the foot end 120. As described herein, the head section 108, the seat section 110, and the foot section 112 of the support frame 106 may be rotatable relative to one another. Thus, the support frame 106 includes one or more actuators 126 for rotating the head section 108 and the foot section 112 relative to the seat section 110. Due to the head section 108, the seat section 110, and the foot section 112 being rotatable relative to one another, each of the sections 108, 110, 112 may be provided with an individual upper surface 114 and an individual lower surface 116 such that the sections 108, 110, 112 may be independently rotated. In embodiments, the upper surface 114 and the lower surface 116 of the support frame 106 define an open interior 128 for housing various components, such as the actuators 126, sensors, processors, communication modules, and the like.

As shown in FIG. 2, a plurality of bracket assemblies 130 are provided on the support frame 106 for securing one or more restraint straps (not shown) to the support frame 106. Specifically, a pair of bracket assemblies 130, each including a restraint bracket 132, are shown mounted to the head end 118 of the support frame 106 at the first side 122 and the second side 124. However, it should be appreciated that any number of bracket assemblies 130 may be provided. For example, additional bracket assemblies 130 may be mounted to the foot end 120 of the support frame 106 at the first side 122 and the second side 124. Additionally, any number of bracket assemblies 130 may be mounted to the support frame 106 along the head end 118, the foot end 120, the first side 122, or the second side 124 of the support frame 106. As discussed in more detail herein, the restraint bracket 132 of each bracket assembly 130 is mounted to the lower surface 116 of the support frame 106 and may be used to secure a restraint strap to the support frame 106. The restraint strap may be any suitable restraint member, such as a band, buckle, and the like, having an end that can be looped, tied, or otherwise secured around a portion of the restraint bracket 132, as discussed in more detail herein.

Figure 3:
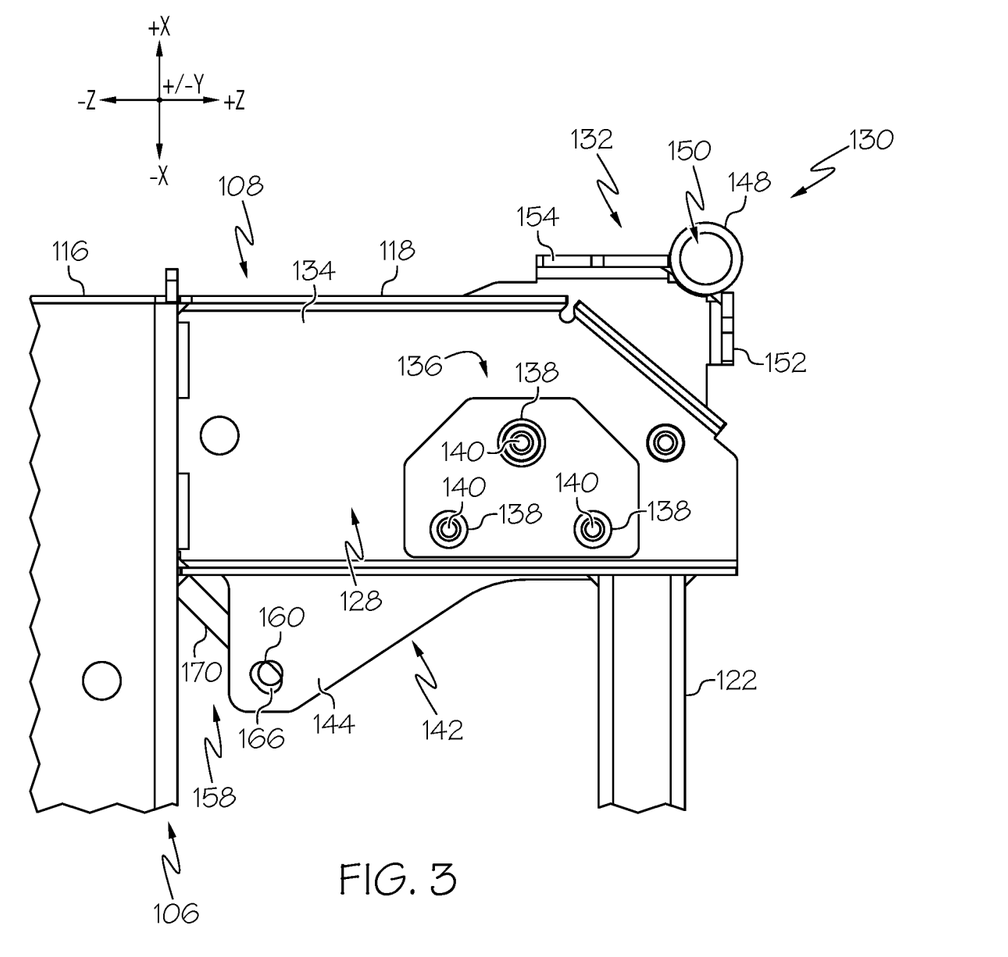
FIG. 3 schematically depicts a partial top view of the support frame of FIG. 2 including a bracket assembly, according to one or more embodiments shown and described herein.

Referring now to FIG. 3, a portion of the head section 108 of the support frame 106 is illustrated with the upper surface 114 of the support frame 106 removed from the lower surface 116 of the support frame 106, thereby exposing the open interior 128 of the support frame 106 and an interior side 134 of the lower surface 116. The bracket assembly 130 includes the restraint bracket 132 and a reinforcement plate 136. The reinforcement plate 136 is provided within the open interior 128 of the support frame 106 and is secured against the interior side 134 of the lower surface 116 of the support frame 106 opposite the restraint bracket 132. The reinforcement plate 136 has one or more plate holes 138 formed therein for receiving fasteners 140 extending through the restraint bracket 132. Thus, the reinforcement plate 136 functions as a washer for further securing the restraint bracket 132 to the support frame 106 and distributing a force across the support frame 106 that results from pulling on the restraint bracket 132, via the restraint strap, away from the lower surface 116 of the support frame 106. As shown, the reinforcement plate 136 has a trapezoidal shape. However, it should be appreciated that the reinforcement plate 136 may have any suitable shape such as circular, rectangular, and the like.

Referring still to FIG. 3, the restraint bracket 132 includes a bracket body 142 having an upper surface 144 and a lower surface 146 (FIG. 4) opposite the upper surface 144. In embodiments, the restraint bracket 132 also includes a line manager socket 148 formed on the upper surface 144 of the bracket body 142. The line manager socket 148 may be a hollow member having a bore 150 formed therethrough and extending through the bracket body 142. The line manager socket 148 receives a line manager that organizes one or more medical lines, such as an intravenous (IV) line from a fluid supply, to a person positioned atop the support frame 106. In embodiments, the line manager socket 148 may be a one-piece, monolithic structure formed with the bracket body 142. As such, the line manager socket 148 may be formed by extruding or folding a portion of the bracket body 142 during formation. As shown, the line manager socket 148 may be a tubular member. However, the line manager socket 148 may have any other suitable shape. In embodiments, the line manager socket 148 may extend perpendicular to the upper surface 144 of the bracket body 142 or, in other embodiments, the line manager socket 148 may extend from the upper surface 144 of the bracket body 142 at an acute angle toward an edge of the bracket body 142.

Referring still to FIG. 3, a first flange 152 and a second flange 154 are also formed on the upper surface 144 of the bracket body 142. In embodiments, the flanges 152, 154 may each be a one-piece, monolithic structure with the bracket body 142 and/or the line manager socket 148. In embodiments, the flanges 152, 154 extend from the line manager socket 148 along a respective side or end of the support frame 106. For example, in embodiments, the first flange 152 extends along the first side 122 of the support frame 106 and the second flange 154 extends along the head end 118 of the support frame 106. Thus, in embodiments in which the support frame 106 has a rectangular shape and the head end 118 extends perpendicular to the first side 122, the first flange 152 and the second flange 154 may extend perpendicular to one another. Accordingly, the first flange 152 and the second flange 154 serve as a rib to the line manager socket 148 so that the line manager socket 148 can withstand misuse load of the line manager being pulled. Additionally, a rectangular mattress or other topper positioned on the support frame 106 may be received between the flanges 152, 154 to further secure the mattress in position. However, in embodiments, an angle between the first flange 152 and the second flange 154 may be less than or greater than 90 degrees. For example, the angle between the first flange 152 and the second flange 154 may be between 30 degrees and 180 degrees, for example when the restraint bracket 132 is positioned along the first side 122 of the support frame 106 and both flanges 152, 154 extend parallel to the first side 122. As shown, it should be appreciated that the flanges 152, 154 extend from and are in contact with the line manager socket 148 to serve as a rib. However, in embodiments, one or both of the flanges 152, 154 may be spaced apart from the line manager socket 148.

Figure 4:
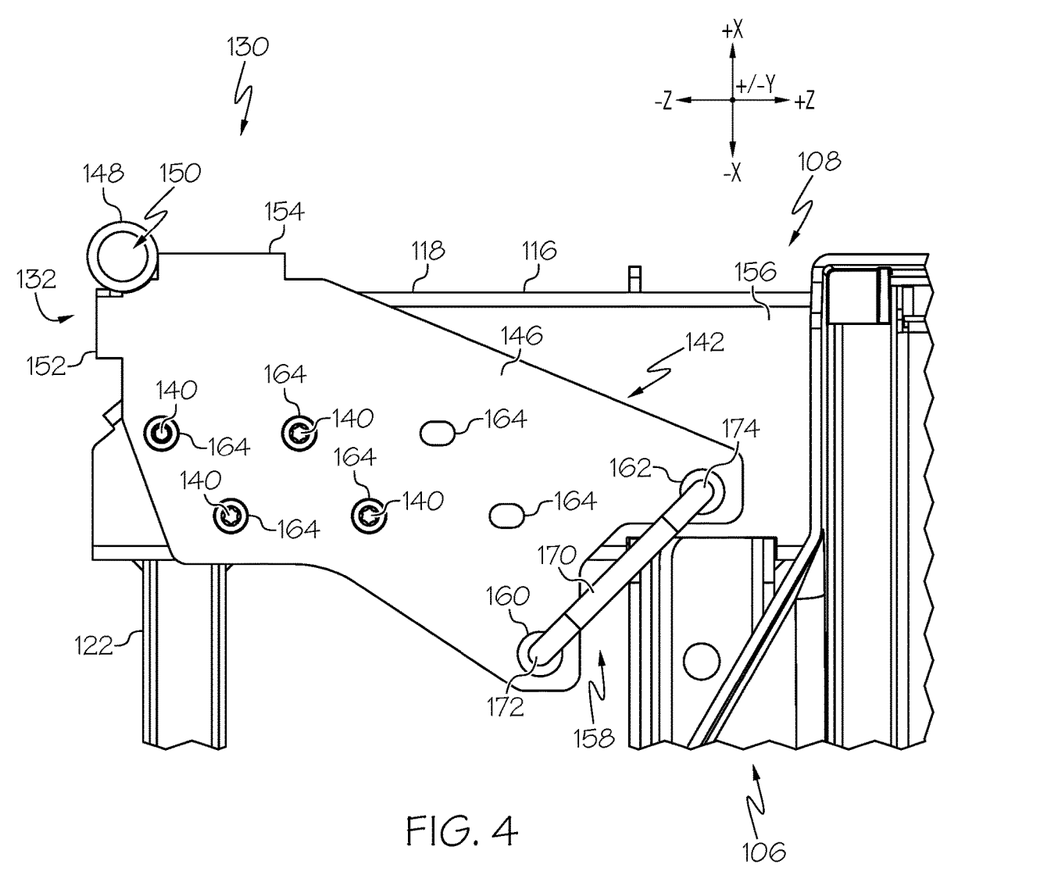
FIG. 4 schematically depicts a partial bottom view of the support frame of FIG. 2 and the bracket assembly, according to one or more embodiments shown and described herein.

Referring now to FIG. 4, a partial view of the head section 108 of the support frame 106 is illustrated as viewed from an exterior side 156 of the lower surface 116 of the support frame 106 opposite the interior side 134 of the lower surface 116 illustrated in FIG. 3. As shown, the restraint bracket 132 further includes an attachment member 158 extending from the lower surface 146 of the bracket body 142. As described in more detail herein, the attachment member 158 is fixed to the lower surface 146 of the bracket body 142 at a first mount portion 160 and a second mount portion 162. In embodiments, the attachment member 158 may be a one-piece, monolithic structure with the bracket body 142. As shown, a plurality of bracket holes 164 are formed in the bracket body 142 through which the fasteners 140 extend to secure the restraint bracket 132 to the support frame 106. As described above, the reinforcement plate 136 (FIG. 3) has a plurality of plate holes 138 each aligning with a corresponding bracket hole 164 for receiving a fastener 140 extending therethrough. As described in more detail herein, the restraint bracket 132 is mounted to the support frame 106 such that the attachment member 158 is oriented inwardly toward a center of the support frame 106. More particularly, the first mount portion 160 and the second mount portion 162 of the attachment member 158 are spaced apart from the head end 118 and the first side 122 of the support frame 106 so that the attachment member 158 is further out of reach from a person positioned atop the support frame 106. Additionally, the second mount portion 162 is positioned so as to avoid trapping and/or pinching of a person's foot when the person support apparatus 100 is in a lowered/collapsed position, e.g., when the lift member lowers the support frame 106 to the base frame 102. While only the bracket assembly 130 positioned at the head end 118 and the first side 122 of the support frame 106 is illustrated and described in detail herein, it should be appreciated that the opposite bracket assembly 130 positioned at the head end 118 and the second side 124 of the support frame 106 is identical in structure except is a mirror image.

Figure 5:
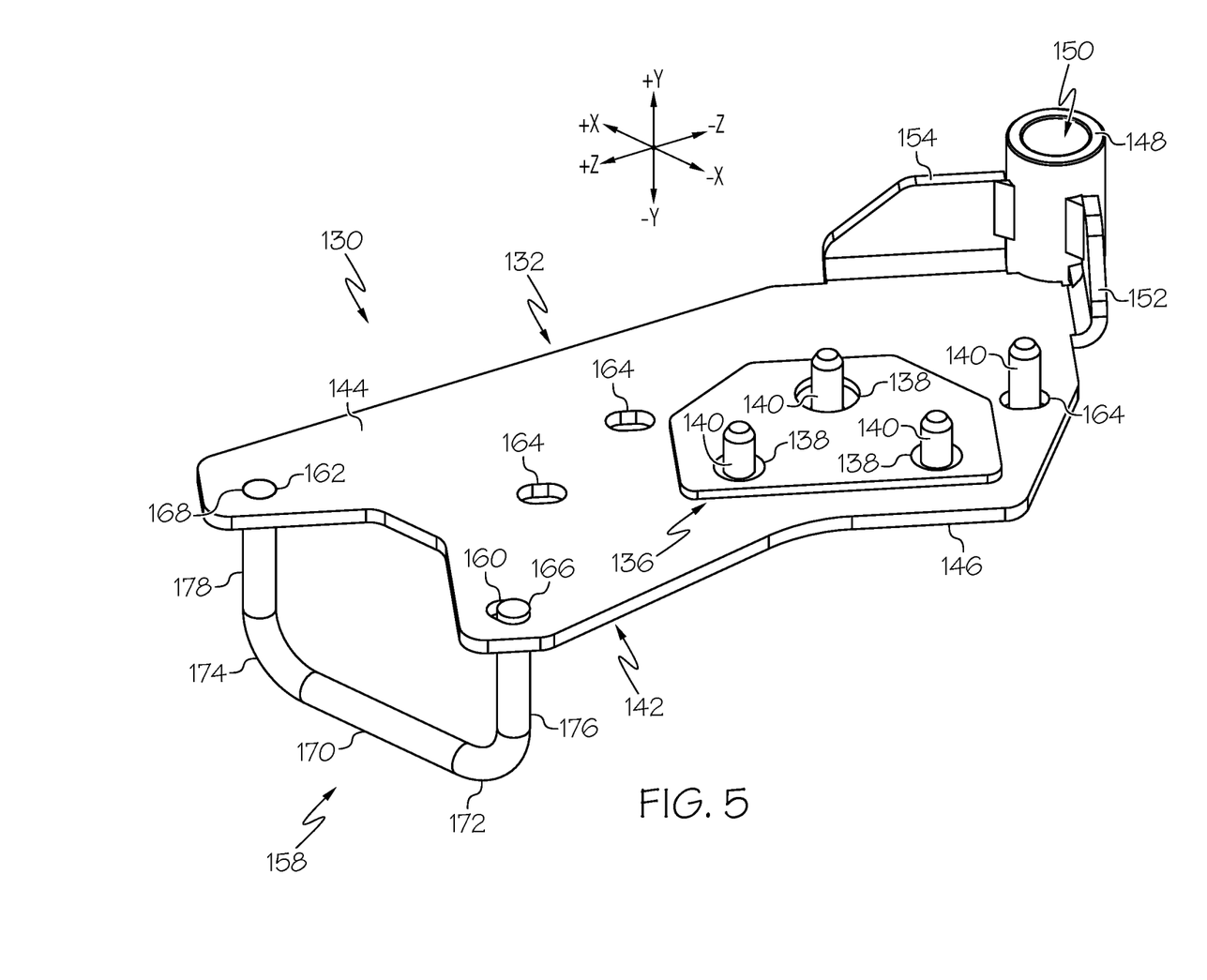
FIG. 5 schematically depicts a top perspective view of the bracket assembly of FIG. 3, according to one or more embodiments shown and described herein.

Referring now to FIG. 5, a perspective view of the bracket assembly 130 is shown apart from the person support apparatus 100. The attachment member 158 has a first end 166 fixed to the lower surface 146 of the bracket body 142 at the first mount portion 160, and a second end 168 opposite the first end 166 fixed to the lower surface 146 of the bracket body 142 at the second mount portion 162. The attachment member 158 includes a bar 170 having a first end 172 and a second end 174 opposite the first end 172, a first leg 176 extending from the first end 172 of the bar 170 to the first mount portion 160 at the lower surface 146 of the bracket body 142, and a second leg 178 extending from the second end 174 of the bar 170 to the second mount portion 162 at the lower surface 146 of the bracket body 142. The first mount portion 160 defines a point at which the attachment member 158, specifically the first leg 176 of the attachment member 158, is joined to the bracket body 142, and the second mount portion 162 defines a point at which the attachment member 158, specifically the second leg 178 of the attachment member 158, is joined to the bracket body 142. Accordingly, the attachment member 158 may be U-shaped. However, the attachment member 158 may have any suitable shape such as V-shaped, W-shaped, a serpentine shape, and the like. As shown, the length of the first leg 176 and the second leg 178 are the same. However, in embodiments, the length of the first leg 176 may be longer or shorter than the length of the second leg 178. In use, a restraint strap is secured to one or more of the bar 170, the first leg 176, and/or the second leg 178 such as by looping an end of the restraint strap around a portion of the attachment member 158, thereby securing the restraint strap to the restraint bracket 132 and the support frame 106 to which the restraint bracket 132 is attached.

It should be appreciated that a fastener 140 does not need to be provided to extend through each bracket hole 164 and plate hole 138 when securing the restraint bracket 132 to the support frame 106. Rather, additional bracket holes 164 may be provided for adjusting a position in which the restraint bracket 132 is attached to the support frame 106. Additionally, the plate holes 138 formed in the reinforcement plate 136 may correspond to any number or arrangement of bracket holes 164 such that the reinforcement plate 136 may be repositioned on the upper surface 144 of the bracket body 142 to further secure the restraint bracket 132 to the support frame 106.

Figure 6:
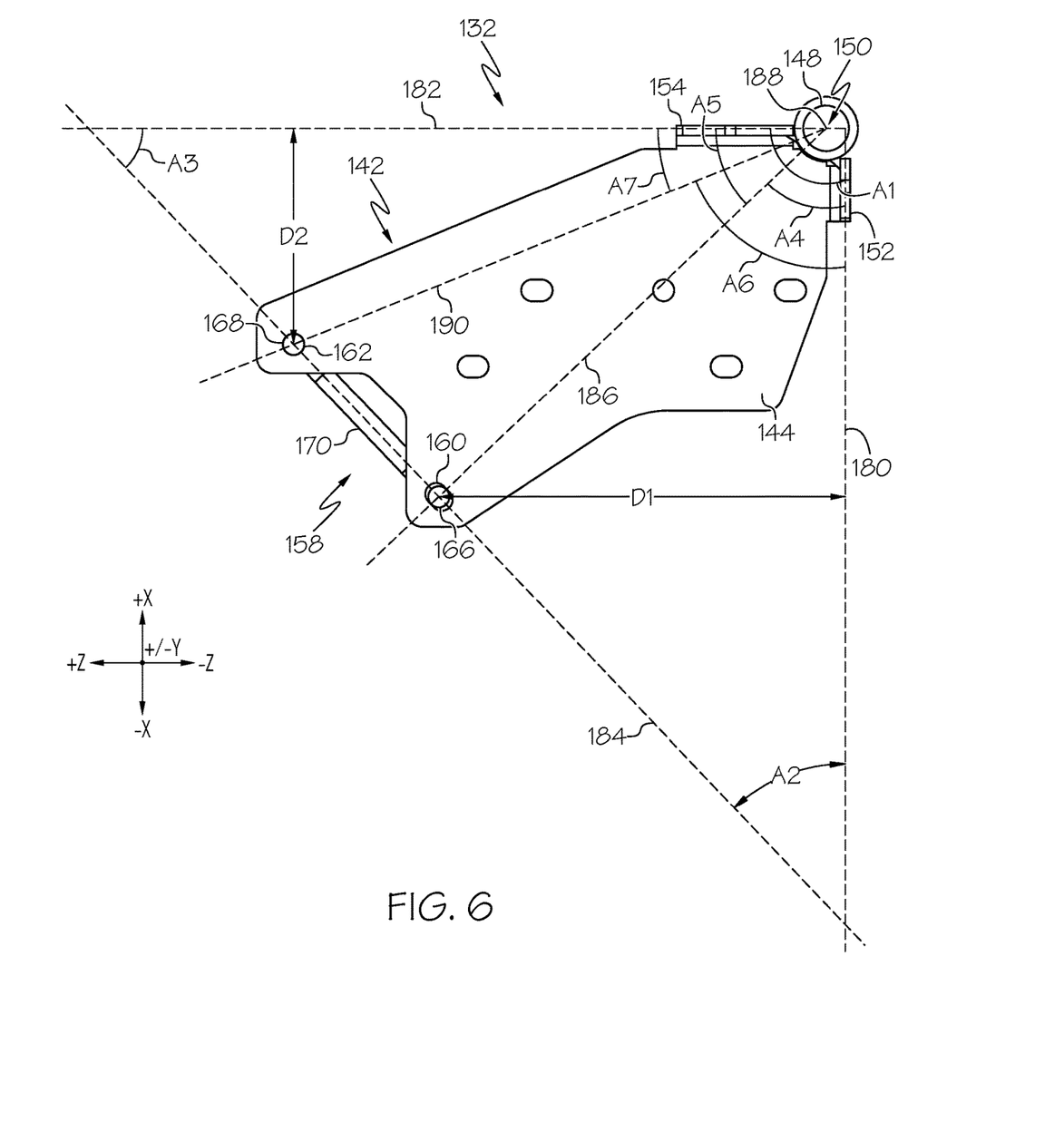
FIG. 6 schematically depicts a top view of a restraint bracket of the bracket assembly of FIG. 3, according to one or more embodiments shown and described herein.
Figure 7:
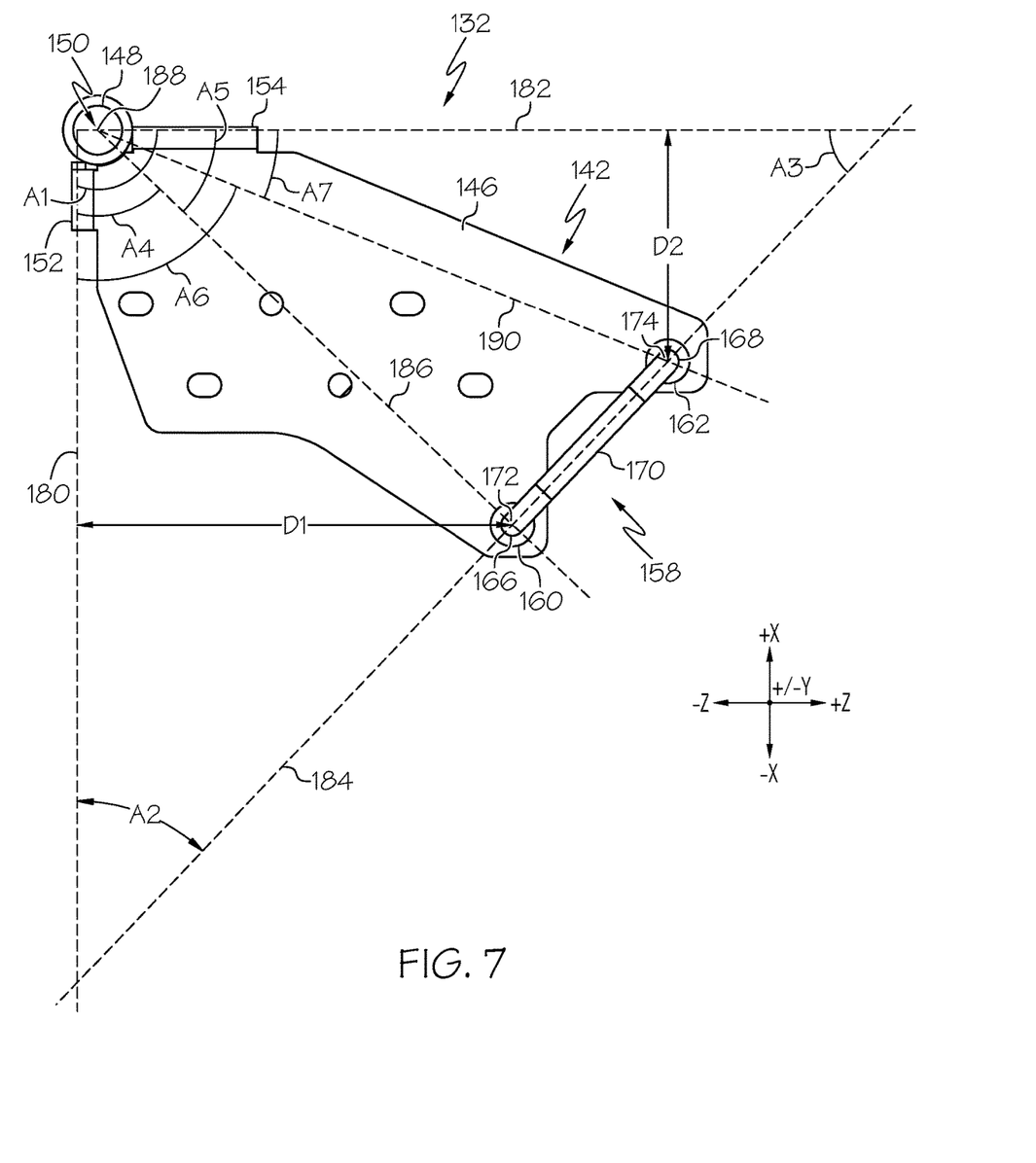
FIG. 7 schematically depicts a bottom view of the restraint bracket of FIG. 6, according to one or more embodiments shown and described herein.

Referring now to FIGS. 6 and 7, the restraint bracket 132 is shown separate from the support frame 106 and the reinforcement plate 136. The first flange 152 defines a first flange axis 180 and the second flange 154 defines a second flange axis 182. The first flange axis 180 defines a first flange plane extending perpendicular to the bracket body 142 and the second flange axis 182 defines a second flange plane extending perpendicular to the bracket body 142. In embodiments described herein, the first flange 152 is perpendicular to the second flange 154 such that a first angle A1 between the first flange axis 180 and the second flange axis 182 is 90 degrees. In embodiments, the first angle A1 may be less than or greater than 90 degrees.

As noted herein, the attachment member 158 extends from the lower surface 146 of the bracket body 142 at the first mount portion 160 and the second mount portion 162. The first leg 176 and the second leg 178 are not illustrated in FIGS. 6 and 7 as the first leg 176 and the second leg 178 are hidden from view by the bracket body 142 in FIG. 6 and the bar 170 in FIG. 7. The bar 170 of the attachment member 158 defines a bar axis 184 extending between the first leg 176 and the second leg 178 and, thus, intersects the first mount portion 160 and the second mount portion 162. The bar axis 184 intersects the first flange axis 180 at a second angle A2. In embodiments, the second angle A2 is between 30 degrees and 60 degrees. In embodiments, the second angle A2 is between 40 degrees and 50 degrees. The bar axis 184 also intersects the second flange axis 182 at a third angle A3. In embodiments, the third angle A3 is between 30 degrees and 60 degrees. In embodiments, the third angle A3 is between 40 degrees and 50 degrees. It should be appreciated that, in embodiments in which the first flange 152 and the second flange 154 are perpendicular to one another, the second angle A2 and the third angle A3 are complementary angles such that the sum of the second angle A2 and the third angle A3 is 90 degrees.

A first mount axis 186 extends from the first mount portion 160 to the line manager socket 148, particularly a center axis 188 of the line manager socket 148 extending coaxial with the bore 150 formed in the line manager socket 148. The first mount axis 186 intersects the center axis 188 of the line manager socket 148 at a fourth angle A4 relative to the first flange axis 180. In embodiments, the fourth angle A4 is between 30 degrees and 60 degrees. In embodiments, the fourth angle A4 is between 40 degrees and 50 degrees. The first mount axis 186 also intersects the center axis 188 of the line manager socket 148 at a fifth angle A5 relative to the second flange axis 182. In embodiments in which the line manager socket 148 is not provided, the first mount axis 186 extends from between the first flange 152 and the second flange 154, particularly a medial portion of a gap formed between the first flange 152 and the second flange 154. It should be appreciated that, in embodiments in which the first flange 152 and the second flange 154 are perpendicular to one another, the fourth angle A4 and the fifth angle A5 are complementary angles such that the sum of the fourth angle A4 and the fifth angle A5 is 90 degrees. The first mount portion 160 is spaced apart from the first flange axis 180, i.e., the first flange plane, by a first distance D1. In embodiments, the first distance D1 is greater than one inch. In embodiments, the first distance D1 is greater than two inches. It should be appreciated that the first distance D1 may be increased by increasing the fourth angle A4 and/or increasing the distance between the first mount portion 160 and the center axis 188 of the line manager socket 148, i.e., the length of the first mount axis 186. It should be appreciated that the first mount portion 160 being spaced apart from the first flange axis 180 by the first distance D1 places the attachment member 158 further out of reach from the person supported on the support frame 106 of the person support apparatus 100. Specifically, the first distance D1 separating the first mount portion 160 from the first flange axis 180 moves the attachment member 158 inwardly toward a center of the support frame 106 placing the attachment member 158 further from the first side 122 of the support frame 106 and further out of reach of the person.

Similarly, a second mount axis 190 extends from the second mount portion 162 to the line manager socket 148, particularly the center axis 188 of the line manager socket 148. The second mount axis 190 intersects the center axis 188 of the line manager socket 148 at a sixth angle A6 relative to the first flange axis 180. In embodiments, the sixth angle A6 is between 50 degrees and 80 degrees. In embodiments, the sixth angle A6 is between 60 degrees and 70 degrees. The second mount axis 190 also intersects the center axis 188 of the line manager socket 148 at a seventh angle A7 relative to the second flange axis 182. In embodiments in which the line manager socket 148 is not provided, the second mount axis 190 extends from between the first flange 152 and the second flange 154, particularly a medial portion of a gap formed between the first flange 152 and the second flange 154. It should be appreciated that, in embodiments in which the first flange 152 and the second flange 154 are perpendicular to one another, the sixth angle A6 and the seventh angle A7 are complementary angles such that the sum of the sixth angle A6 and the seventh angle A7 is 90 degrees. The second mount portion 162 is spaced apart from the second flange axis 182, i.e., the second flange plane, by a second distance D2. In embodiments, the second distance D2 is greater than one inch. In embodiments, the second distance D2 is less than the first distance D1. It should be appreciated that the second distance D2 may be increased by decreasing the sixth angle A6 and/or increasing the distance between the second mount portion 162 and the center axis 188 of the line manager socket 148, i.e., the length of the second mount axis 190. It should be appreciated that the second mount portion 162 being spaced apart from the second flange axis 182 by the second distance D2 places the attachment member 158 further out of reach from the person supported on the support frame 106 of the person support apparatus 100. Specifically, the second distance D2 separating the second mount portion 162 from the second flange axis 182 moves the attachment member 158 inwardly toward a center of the support frame 106 placing the attachment member 158 further from the head end 118 of the support frame 106 and further out of reach of the person.

From the above, it is to be appreciated that defined herein are person support apparatuses including a bracket assembly. The bracket assembly includes a restraint bracket for restraining a person to a support frame in an arm-up position such that that arm or arms of the person may be restrained while extending in a direction toward the head of the person rather than along the person's side toward the person's feet. The restraint bracket includes a bracket body, a line manager socket formed on an upper surface of the bracket body, a pair of flanges formed on the upper surface of the bracket body, and an attachment member extending from a lower surface of the bracket body. The attachment member is positioned on the lower surface of the bracket body and spaced apart from a pair of flange axes defined by the pair of flanges to be positioned inwardly relative to the support frame. By positioning the attachment member inwardly relative to the support frame, the ability of a person positioned atop the support frame to access the attachment member is inhibited.

Clause 1. A restraint bracket comprising: a bracket body having an upper surface and a lower surface opposite the upper surface; a pair of flanges formed on the upper surface of the bracket body; and an attachment member extending from the lower surface of the bracket body, the attachment member having a first end and a second end opposite the first end, the first end and the second end fixed to the lower surface of the bracket body.

Clause 2. The restraint bracket of clause 1, further comprising a line manager socket formed on the upper surface of the bracket body, the pair of flanges extending from the line manager socket.

Clause 3. The restraint bracket of clause 1 or clause 2, wherein the attachment member comprises: a bar having a first end and a second end opposite the first end; a first leg extending from the first end of the bar to the lower surface of the bracket body at a first mount portion; and a second leg extending from the second end of the bar to the lower surface of the bracket body at a second mount portion.

Clause 4. The restraint bracket of clause 3, wherein: the pair of flanges includes: a first flange defining a first flange axis; and a second flange defining a second flange axis perpendicular to the first flange axis; and the bar defines a bar axis, the bar axis extending at an angle between 20 degrees and 70 degrees from the first flange axis.

Clause 5. The restraint bracket of clause 4, wherein the bar axis extends at an angle between 30 degrees and 60 degrees from the first flange axis.

Clause 6. The restraint bracket of clause 4 or clause 5, wherein a first mount axis extends from between the pair of flanges to the first mount portion, the first mount axis extending at an angle between 30 degrees and 60 degrees from the first flange axis.

Clause 7. The restraint bracket of any of clauses 4-6, wherein a second mount axis extends from between the pair of flanges to the second mount portion, the second mount axis extending at an angle between 50 degrees and 80 degrees from the first flange axis.

Clause 8. The restraint bracket of any of clauses 4-7, wherein: the first flange axis defines a first flange plane extending perpendicular to the bracket body; and the first mount portion is spaced apart from the first flange plane by a distance of at least one inch.

Clause 9. A bracket assembly comprising: a restraint bracket comprising: a bracket body having an upper surface and a lower surface opposite the upper surface, a plurality of bracket holes formed in the bracket body; a pair of flanges formed on the upper surface of the bracket body; and an attachment member extending from the lower surface of the bracket body, the attachment member having a first end and a second end opposite the first end, the first end and the second end fixed to the lower surface of the bracket body; a reinforcement plate having a plurality of plate holes corresponding to the plurality of bracket holes; and a plurality of fasteners extending through the plurality of bracket holes and the plurality of plate holes for attaching the reinforcement plate to the restraint bracket.

Clause 10. The bracket assembly of clause 9, wherein the attachment member is U-shaped.

Clause 11. The bracket assembly of clause 9 or clause 10, wherein the attachment member comprises: a bar having a first end and a second end opposite the first end; a first leg extending from the first end of the bar to the lower surface of the bracket body at a first mount portion; and a second leg extending from the second end of the bar to the lower surface of the bracket body at a second mount portion.

Clause 12. The bracket assembly of clause 11, wherein the pair of flanges includes: a first flange defining a first flange axis; and a second flange defining a second flange axis perpendicular to the first flange axis.

Clause 13. The bracket assembly of clause 12, wherein a first mount axis extends from between the pair of flanges to the first mount portion, the first mount axis extending at an angle between 30 and 60 degrees from the first flange axis.

Clause 14. The bracket assembly of clause 12 or clause 13, wherein a second mount axis extends from between the pair of flanges to the second mount portion, the second mount axis extending at an angle between 60 degrees and 80 degrees from the first flange axis.

Clause 15. The bracket assembly of any of clauses 12-14, wherein: the first flange axis defines a first flange plane extending perpendicular to the bracket body; and the first mount portion is spaced apart from the first flange plane by a distance of at least one inch.

Clause 16. A person support apparatus comprising: a support frame having an upper surface and a lower surface opposite the upper surface; and a restraint bracket mounted to the lower surface of the support frame, the restraint bracket comprising: a bracket body having an upper surface and a lower surface opposite the upper surface; a pair of flanges formed on the upper surface of the bracket body; and an attachment member extending from the lower surface of the bracket body, the attachment member having a first end and a second end opposite the first end, the first end and the second end fixed to the lower surface of the bracket body.

Clause 17. The person support apparatus of clause 16, wherein: the support frame defines an open interior between the upper surface and the lower surface of the support frame; a reinforcement plate is positioned within the open interior of the support frame on an opposite side of the lower surface than the restraint bracket; one or more fasteners extending through the restraint bracket, the lower surface of the support frame, and the reinforcement plate to fix the reinforcement plate to the restraint bracket.

Clause 18. The person support apparatus of clause 16 or clause 17, wherein the pair of flanges includes: a first flange defining a first flange axis; and a second flange defining a second flange axis perpendicular to the first flange axis.

Clause 19. The person support apparatus of clause 18, wherein: a first mount axis extends from between the pair of flanges to the first end of the attachment member, the first mount axis extending at an angle between 30 and 60 degrees from the first flange axis; and a second mount axis extends from between the pair of flanges to the second end of the attachment member, the second mount axis extending at an angle between 60 degrees and 80 degrees from the first flange axis.

Clause 20. The person support apparatus of any of clauses 16-19, further comprising: a base frame on which the support frame is positioned; and one or more actuators configured to rotate at least a portion of the support frame relative to the base frame.

It will be apparent to those skilled in the art that various modifications and variations can be made to the embodiments described herein without departing from the scope of the claimed subject matter. Thus, it is intended that the specification cover the modifications and variations of the various embodiments described herein provided such modification and variations come within the scope of the appended claims and their equivalents.

What is claimed is:

1. A restraint bracket comprising:
a bracket body having an upper surface and a lower surface opposite the upper surface;
an attachment member extending from the lower surface of the bracket body, the attachment member having a first end and a second end opposite the first end, the first end and the second end fixed to the lower surface of the bracket body,
the attachment member comprising:
a bar having a first end and a second end opposite the first end, the bar defining a bar axis;
a first leg extending from the first end of the bar to the lower surface of the bracket body at a first mount portion; and
a second leg extending from the second end of the bar to the lower surface of the bracket body at a second mount portion; and
a pair of flanges formed on the upper surface of the bracket body, the pair of flanges comprising:
a first flange defining a first flange axis; and
a second flange defining a second flange axis perpendicular to the first flange axis,
the bar axis extending at an angle between 20 degrees and 70 degrees from the first flange axis.

2. The restraint bracket of claim 1, further comprising a line manager socket formed on the upper surface of the bracket body, the pair of flanges extending from the line manager socket.

3. The restraint bracket of claim 1, wherein the bar axis extends at an angle between 30 degrees and 60 degrees from the first flange axis.

4. The restraint bracket of claim 1, wherein a first mount axis extends from between the pair of flanges to the first mount portion, the first mount axis extending at an angle between 30 degrees and 60 degrees from the first flange axis.

5. The restraint bracket of claim 1, wherein a second mount axis extends from between the pair of flanges to the second mount portion, the second mount axis extending at an angle between 50 degrees and 80 degrees from the first flange axis.

6. The restraint bracket of claim 1, wherein:
the first flange axis defines a first flange plane extending perpendicular to the bracket body; and
the first mount portion is spaced apart from the first flange plane by a distance of at least one inch.

7. A bracket assembly comprising:
a restraint bracket comprising:
a bracket body having an upper surface and a lower surface opposite the upper surface, a plurality of bracket holes formed in the bracket body;
an attachment member extending from the lower surface of the bracket body, the attachment member having a first end and a second end opposite the first end, the first end and the second end fixed to the lower surface of the bracket body, the attachment member comprising:
a bar having a first end and a second end opposite the first end, the bar defining a bar axis;
a first leg extending from the first end of the bar to the lower surface of the bracket body at a first mount portion; and
a second leg extending from the second end of the bar to the lower surface of the bracket body at a second mount portion; and
a pair of flanges formed on the upper surface of the bracket body, the pair of flanges comprising:
a first flange defining a first flange axis; and
a second flange defining a second flange axis perpendicular to the first flange axis,
the bar axis extending at an angle between 20 degrees and 70 degrees from the first flange axis;
a reinforcement plate having a plurality of plate holes corresponding to the plurality of bracket holes; and
a plurality of fasteners extending through the plurality of bracket holes and the plurality of plate holes for attaching the reinforcement plate to the restraint bracket.

8. The bracket assembly of claim 7, wherein the attachment member is U-shaped.

9. The bracket assembly of claim 7, wherein a first mount axis extends from between the pair of flanges to the first mount portion, the first mount axis extending at an angle between 30 and 60 degrees from the first flange axis.

10. The bracket assembly of claim 7, wherein a second mount axis extends from between the pair of flanges to the second mount portion, the second mount axis extending at an angle between 60 degrees and 80 degrees from the first flange axis.

11. The bracket assembly of claim 7, wherein:
the first flange axis defines a first flange plane extending perpendicular to the bracket body; and
the first mount portion is spaced apart from the first flange plane by a distance of at least one inch.

12. A person support apparatus comprising:
a support frame having an upper surface and a lower surface opposite the upper surface; and
a restraint bracket mounted to the lower surface of the support frame, the restraint bracket comprising:
a bracket body having an upper surface and a lower surface opposite the upper surface;
an attachment member extending from the lower surface of the bracket body, the attachment member having a first end and a second end opposite the first end, the first end and the second end fixed to the lower surface of the bracket body, the attachment member comprising:
a bar having a first end and a second end opposite the first end, the bar defining a bar axis;
a first leg extending from the first end of the bar to the lower surface of the bracket body at a first mount portion; and
a second leg extending from the second end of the bar to the lower surface of the bracket body at a second mount portion; and
a pair of flanges formed on the upper surface of the bracket body, the pair of flanges comprising:
a first flange defining a first flange axis; and
a second flange defining a second flange axis perpendicular to the first flange axis,
the bar axis extending at an angle between 20 degrees and 70 degrees from the first flange axis.

13. The person support apparatus of claim 12, wherein:
the support frame defines an open interior between the upper surface and the lower surface of the support frame;
a reinforcement plate is positioned within the open interior of the support frame on an opposite side of the lower surface than the restraint bracket;

one or more fasteners extending through the restraint bracket, the lower surface of the support frame, and the reinforcement plate to fix the reinforcement plate to the restraint bracket.

14. The person support apparatus of claim 12, wherein:
a first mount axis extends from between the pair of flanges to the first end of the attachment member, the first mount axis extending at an angle between 30 and 60 degrees from the first flange axis; and
a second mount axis extends from between the pair of flanges to the second end of the attachment member, the second mount axis extending at an angle between 60 degrees and 80 degrees from the first flange axis.

15. The person support apparatus of claim 12, further comprising:
a base frame on which the support frame is positioned; and
one or more actuators configured to rotate at least a portion of the support frame relative to the base frame.

* * * * *